US005798412A

United States Patent [19]

Sanderson et al.

[11] Patent Number: 5,798,412
[45] Date of Patent: Aug. 25, 1998

[54] ALKYLENE GLYCOL PRODUCTION USING CARBON CATALYSTS

[75] Inventors: John R. Sanderson; Edward T. Marquis, both of Austin, Tex.

[73] Assignee: Huntsman Petrochemical Corporation, Austin, Tex.

[21] Appl. No.: 895,286

[22] Filed: Jul. 16, 1997

[51] Int. Cl.$^6$ .............................. C08K 3/00; C08G 59/00
[52] U.S. Cl. .................. 524/847; 524/705; 524/787; 524/800; 524/847; 528/403; 528/408; 528/421; 528/425; 568/606; 568/701
[58] Field of Search ................. 524/705, 787, 524/800, 847; 528/403, 408, 421, 425; 568/606, 701

[56] References Cited

U.S. PATENT DOCUMENTS

| | | | |
|---|---|---|---|
| 3,970,711 | 7/1976 | Reiche et al. | 260/635 E |
| 4,385,190 | 5/1983 | Ohashi et al. | 568/603 |
| 4,391,994 | 7/1983 | Kogoma et al. | 568/593 |
| 4,579,983 | 4/1986 | Keen | 568/867 |
| 4,701,571 | 10/1987 | Soo et al. | 568/867 |
| 4,760,200 | 7/1988 | Keen et al. | 568/867 |
| 5,034,134 | 7/1991 | George et al. | 210/651 |
| 5,260,495 | 11/1993 | Forkner | 568/867 |

FOREIGN PATENT DOCUMENTS

0160330A1  11/1985  European Pat. Off. .
WO 95/20559  8/1995  WIPO .

*Primary Examiner*—Samuel A. Acquah
*Attorney, Agent, or Firm*—Arnold, White & Durkee

[57] ABSTRACT

A process in which carbon is used to catalyze production of alkylene glycols from alkylene oxides and water. Using this process, carbon may be employed to selectively catalyze the hydrolysis of alkylene oxides, such as ethylene oxide, to monoalkylene gylcols, such as monoethylene glycol. Typically, activated carbon is employed. Suitable forms of activated carbon or other carbon material include powders, granulates, extruded shapes, or mixtures thereof. The process may be carried out as a continuous or batch reaction process.

22 Claims, No Drawings

ALKYLENE GLYCOL PRODUCTION USING CARBON CATALYSTS

BACKGROUND OF THE INVENTION

1. Field of the Invention

This invention relates generally to production of alkylene glycols from alkylene oxides and water and, more specifically, to catalyzed production of alkylene glycols. In particular, this invention relates to selective production of monoalkylene glycols using a carbon catalyst, such as activated carbon.

2. Description of the Related Art

Alkylene glycols such as ethylene glycol and propylene glycol are typically produced by hydration of a corresponding alkylene oxide. Besides monoalkylene glycols, such reactions typically yield polyalkylene glycols, including dialkylene glycols and trialkylene glycols. When monoalkylene glycols are the desired product, a large molar excess of water is typically employed in order to achieve selectivity to a monoglycol product. However, separation of alkylene glycol product from large amounts of water, typically requires a substantial amount of energy. Such separation is typically performed by evaporation of water and distillation of the desired product from the evaporation residue.

In an attempt to reduce the requirement for large amounts of water in the production of monoalkylene glycols, selective hydration catalysts have been developed. In the presence of these catalysts, the selectivity of alkylene glycol production is typically increased with respect to monoalkylene glycol in the presence of reduced amounts of water. Typical selective hydration catalysts include, for example, metalate anions supported on a solid anionic exchange resin.

Processes employing traditional selective hydration catalysts suffer from several disadvantages. For example, metalate anion-containing materials are typically expensive, and require that anions be coordinated or exchanged on electropositive complexing sites of a solid support. These anion materials may be prone to removal or leaching from a solid support, thus requiring methods and apparatus for recovering lost anions from the hydrolysis products. In addition, means of regenerating ionic materials onto a catalytic support are also typically required. Furthermore, a resin support, such as cross linked polystyrene may not be stable under conditions of a hydrolysis reaction. Therefore, disadvantages associated with conventional selective hydration catalysts add to the complexity and cost of hydrolysis reactions to produce alkylene glycols.

In the past, attempts have been made to enhance the stability of selective hydration catalysts by the addition of small quantities of anions, such as metalate anions, to a reaction mixture in order to replace anions lost from the electropositive complexing sites during the course a of reaction. However, this practice adds to the expense and complexity of a hydration process.

SUMMARY OF THE INVENTION

In one respect, this invention is a process for preparing alkylene glycols, as well as alkylene glycol prepared according to the same, in which alkylene oxide is combined with water in the presence of carbon under conditions such that the carbon catalyzes the reaction of alkylene oxide with water to form alkylene glycol. Typically the carbon is activated carbon, more typically the carbon is activated carbon present in a particulate form. The activated carbon may optionally comprise acid-washed activated carbon. In one embodiment, the alkylene glycol comprises monoethylene glycol, monopropylene glycol, or mixtures thereof, and the alkylene oxide comprises ethylene oxide, propylene oxide, or mixtures thereof In another embodiment, the alkylene oxide and water may be combined in a continuous reaction process.

In another respect, this invention is a process for preparing alkylene glycol products, as well as alkylene glycol products prepared according to the same, in which alkylene oxide is combined with water in the presence of a catalyst material comprising activated carbon under conditions such that the activated carbon catalyzes the reaction of alkylene oxide with water to form alkylene glycol product. In one embodiment, this process may be used to prepare alkylene glycol product that comprises greater than about 70% monoalkylene glycol. In another embodiment, the activated carbon may comprise at least one of coconut carbon, peat carbon, coal carbon, or mixtures thereof. In still another embodiment, the activated carbon may have an internal surface area of from about 500 g/m$^2$ to about 1500 g/m$^2$. In yet another embodiment, the alkylene oxide and water may be combined in a continuous reaction process in which activated carbon is present in a particulate form. In other embodiments, the activated carbon may optionally comprise acid-washed activated carbon. In one typical embodiment, the alkylene glycol comprises monoethylene glycol and the alkylene oxide comprises ethylene oxide. In another typical embodiment, alkylene oxide and water are combined in a molar ratio of from about 1:5 to about 1:20, at a temperature of from about 60° C. to about 160° C., and at a pressure of from about 100 psig to about 1000 psig.

In another respect, this invention is a process for preparing alkylene glycol products, as well as alkylene glycol products prepared according to the same, in which ethylene oxide is combined with water in the presence of activated carbon material under conditions such that the activated carbon material catalyzes the reaction of ethylene oxide with water to form alkylene glycol product. In one embodiment, the alkylene glycol product comprises greater than about 70% monoethylene glycol. In yet another embodiment, ethylene oxide and water are combined in a continuous reaction process. In yet another embodiment the activated carbon has an internal surface area of from about 500 g/m$^2$ to about 1500 g/m$^2$. In yet another embodiment, ethylene oxide and water are combined in a molar ratio of from about 1:5 to about 1:20, at a temperature of from about 60° C. to about 160° C., and at a pressure of from about 100 psig to about 1000 psig.

DESCRIPTION OF ILLUSTRATIVE EMBODIMENTS

Embodiments of the disclosed method address deficiencies in the aforementioned art by providing a method for the selective preparation of monoalkylene glycols by reacting alkylene oxides with water in the presence of an insoluble carbon material, typically activated carbon material. Advantageously, activated carbon and other carbons are commercially available and, in many cases, may be employed as hydrolysis catalysts without further preparation. In addition, activated carbons and other carbons are typically inexpensive and readily available in large quantities. The disclosed method is useful, for among things, the hydrolysis of alkylene oxides such as ethylene oxide to alkylene glycol products, and is particularly useful for producing monoalkylene glycols such as monoethylene glycol. Although alkylene glycol products may include a variety of mono and polyalkylene glycols, in the practice of the disclosed method the production of higher molecular weight polyols, such as diethylene glycol and triethylene glycol, is minimized. Surprisingly, the disclosed method gives high selectivity to monoalkylene glycols using a carbon material without the addition of other catalyst materials, such as ionic materials.

In the practice of the disclosed method, alkylene oxides may be hydrolyzed to alkylene glycols in the presence of carbon. Such a catalyst typically consists essentially of carbon. By "consists essentially of carbon" it is meant that a carbon material capable of functioning as a hydrolysis catalyst has not been processed or otherwise treated to contain other hydrolysis catalyzing materials beyond the materials present in the carbon is in its commercially available or native state. In this regard, any carbon material suitable for catalyzing hydrolysis of alkylene oxides may be employed, although carbon materials having high internal and/or external surface areas are more typically employed. Most typically, carbon materials comprising activated carbon are used. As used herein, "activated carbon" refers to any carbon material having a porous or honeycomb-like internal structure, including, but not limited to, co-derived carbon, pre-derived carbon, or mixtures thereof. Examples of suitable activated carbons include, but are not limited to those carbons obtained by destructive distillation of carbonaceous material such as wood, nutshells, animal bones, coconut, coal, peat moss, and mixtures thereof. Most typically, activated carbon obtained by destructive distillation of coconut is employed. Other acceptable forms of carbon include, but are not limited to, non-activated particulate carbon materials, such as powdered, ground, or otherwise pulverized carbon materials.

Although any carbon material having a surface area suitable for catalyzing hydrolysis of alkylene oxides to alkylene glycols may be employed, activated carbon having an internal surface area of from about 500 to about 1500 square meters per gram (m²/g) is typically employed. For example, in one embodiment activated carbon having an internal surface area of about 929 m²/g and a density of from about 0.08 to about 0.5 may be employed. Typically, carbon is "activated" by heating to from about 800° C. to about 900° C. with steam or carbon dioxide. Specific examples of suitable activated carbons include, but are not limited to, "TIGG CC 1230" and "TIGG AWC 1240" (available from TIGG Corporation of Pittsburgh, Pa.); "PE", "4040, ""207A," and "BT" (available from Barneby & Sutcliffe Corporation of Columbus, Ohio), and "NORITE RO 0.8" (available from Aldrich Chemical of Milwaukee, Wis.). Also suitable as a catalyst in the practice of the disclosed method are acid-washed carbons, for example, carbon washed with any suitable inorganic or organic acid to reduce alkalinity. Most typically, acid washed carbon is an activated carbon washed with a mineral acid such as phosphoric acid, sulfuric acid, etc.

In one embodiment of the practice of the disclosed method, a carbon is typically activated carbon material. In this embodiment, activated carbon may be used in a variety of forms, depending on the particular hydrolysis reaction scheme and equipment employed. In this regard, any form of activated carbon suitable for catalyzing a hydrolysis reaction of alkylene oxide to alkylene glycol may be used in continuous or batch reaction processes. For example, activated carbon may be present in the form of a particulate, such as powder, granules, chips, pellets, extruded shapes, or a mixture thereof. However, size and shape of activated carbon materials may be varied to optimize reaction rate and selectivity. It will also be understood with benefit of the present disclosure that mixtures of activated carbon and/or other types of carbon materials having different sizes and shapes may be employed in either batch or continuous reaction schemes.

In the practice of the disclosed method, any alkylene oxides suitable for hydrolysis to alkylene glycols may be employed. Typical alkylene oxides include those represented by the formula:

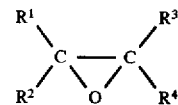

wherein $R^1$, $R^2$, $R^3$, and $R^4$ each represent a hydrogen atom or an optionally substituted alkyl group having from about one to about four carbon atoms, more typically one or two carbon atoms. Of the alkylene oxides encompassed by the above definition, typically those alkylene oxides having a total of about six or less carbon atoms, more typically those having five or less carbon atoms, even more typically those having about four or less carbon atoms, even more typically those having about three or less carbon atoms, and most typically those having about two carbon atoms are employed. For example, in one typical embodiment, $R^1$, $R^2$ and $R^3$ are hydrogen atoms and $R^4$ is an alkyl group having from about 1 to about 3 carbon atoms. In one more typical embodiment, $R^1$, $R^2$, $R^3$, and $R^4$ are hydrogen atoms. Specific examples of suitable alkylene oxides include, but are not limited to, ethylene oxide, propylene oxide, and butylene oxide (including isobutylene oxide, 1,2-butylene oxide, and 2,3-butylene oxide), pentylene oxide, cyclohexene oxide, etc. More typically, butylene oxide, ethylene oxide and/or propylene oxide are employed. Even more typically, ethylene oxide and/or propylene oxide are employed. Most typically, ethylene oxide is employed. Furthermore, it will be understood in each case, mixtures of alkylene oxides are also possible.

Hydrolysis of alkylene oxides is typically performed in the presence of water alone, although other compounds such as ethers or other organic solvents may also be present. Most typically, deionized water or water substantially free of impurities is employed. Although the disclosed method may be practiced utilizing any molar ratio of ethylene oxide to water suitable for supporting hydrolysis, it is typically desirable to employ at least an equimolar portion of water to alkylene oxide, while at the same time minimizing the amount of excess water in order to reduce costs associated with energy and water handling. Typically a ratio of from about 1 to about 30 moles of water per mole of alkylene oxide is employed. More typically a ratio of from about 2.5 to about 25, even more typically from about 5 to about 20, and most typically between about 10 and about 20 moles of water per mole of alkylene oxide is employed. Using the disclosed method, selectivities to monoalkylene glycols is typically greater than about 70%, more typically greater than about 80% and most typically greater than about 90%. It will be understood with benefit of the present disclosure that selectivity to monoalkylene oxides may be varied by controlling the molar ratio of water to alkylene oxide as desired to fit the requirements of an individual application.

Benefits of the disclosed method may be obtained using either a batch or continuous hydrolysis process. Typically a continuous process, with or without recycle of unconsumed reactants, is employed for commercial applications. In addition, the disclosed method may be practiced using a liquid and/or vapor phase hydrolysis reaction conducted in the presence of an activated carbon or other carbon material catalyst. In either case, a mixture of alkylene oxide and water in a liquid, vapor or mixed liquid/vapor state may be contacted with an activated carbon or other carbon material catalyst to catalyze the hydrolysis of the alkylene oxide to alkylene glycol.

The disclosed method may be carried out at any temperature and/or pressure suitable for supporting a hydrolysis reaction. However, in a liquid phase process reaction temperature and pressure are typically selected to maintain liquid reaction conditions. Typically, in the case of continuous or batch reaction schemes, a liquid process is carried out at a temperature of between about 20° C. and about 250° C., more typically between about 60° C. and about 160° C., and most typically between about 80° C. and about 130° C. Typically, such a batch or continuous liquid phase hydrolysis reaction is carried out at a pressure of from about atmospheric to about 10,000 psig, or any other pressure suitable for maintaining a portion of alkylene oxide dissolved in water. More typically, such a reaction is carried out at a pressure from about 25 psig to about 5,000 psig, even more typically from about 100 psig to about 1000 psig, and most typically from about 100 psig to about 500 psig. In any case, the reaction temperature and pressure may be selected to maintain liquid reaction conditions using techniques known in the art. Although a liquid phase hydrolysis reaction may be carried out at any pH, such a reactant system typically has a pH of between about 5 and about 10, and most typically between about 6 and about 8.

In the practice of the disclosed method, a hydrolysis reaction may optionally be carried out in the presence of one or more gases. When a gas is optionally employed, in a continuous process gas is typically present as a diluent, while in a batch process gas is typically present as a gas blanket. Examples of suitable gases include substantially inert gases, such as nitrogen, helium, argon, or mixtures thereof.

In a continuous process of the disclosed method, the mass flow over an activated carbon or other carbon material catalyst may be adjusted to provide a desired hydrolysis rate and selectivity to monoalkylene glycols. Typically, the mass flow is adjusted to provide a sufficient catalyzed reaction time to ensure maximum conversion of alkylene oxide to alkylene glycol by adjusting a variety of parameters in a manner known to those of skill in the art. Such parameters include reaction temperature, amount of reactants, etc. It will be understood with benefit of the present disclosure that the rate of a hydrolysis reaction may be relatively slower and selectivity to monoalkylene glycols relatively higher at reaction temperatures below about 60° C., while a reaction may be relatively faster and selectivity to monoalkylene glycols relatively lower at reaction temperatures above about 160° C.

In a typical continuous process embodiment, carbon material is typically present in one or more reactors or reaction zones. A continuous reactor having at least one heated reactive zone filled with activated carbon is typically employed. A mixture of alkylene oxide and water is typically flowed up through a heated reactor bed at a flow rate sufficient to provide a reaction time sufficient to obtain the desired conversion of alkylene oxide to alkylene glycol. Liquid space velocities are typically maintained from about 0.5 to about 5 g/($cm^3$ of catalyst)(hr), although any suitable liquid space velocity may be employed. In the case of a continuous reaction process, any type and form of carbon suitable for catalyzing hydrolysis may be employed, including any of those types listed previously. However, in such a continuous reaction system, activated carbon is typically employed. Most typically in such a system, activated carbon is of coconut C type and is typically present in a granular or extruded form.

Any size of activated carbon or other carbon material may be employed in a continuous process that is suitable for catalyzing hydrolysis of alkylene oxide to alkylene glycols. However, the size of activated carbon and other carbon materials is typically selected to optimize production of alkylene oxide for a particular application. For example, smaller carbon materials provide more catalyst surface area but produce a larger pressure drop across a reactive zone. Larger carbon materials provide less catalyst surface area and produce less pressure drop, but may require a larger reactor and/or lower reactant flow rate. Typically an activated carbon catalyst material having an average particle size of from about 4×10 mesh to about 12×40 mesh is employed, though activated carbons having larger and smaller average particle size also may be used. Other suitable examples include, but are not limited to, $\frac{1}{8}$" pelleted, $\frac{1}{16}$" pelleted, and $\frac{1}{16}$" extruded particles.

In a typical batch reaction process, water and alkylene oxide are combined with activated carbon material in a batch reactor, such as an autoclave, and heated for a sufficient period of time for the reaction of alkylene oxide to alkylene glycol, typically for greater than about 2 hours, more typically for less than about 4 hours, and most typically from about 2 to about 4 hours. In one embodiment, such a batch reaction is carried out at a temperature of from about 80° C. to about 140° C., and most typically at a temperature of from about 80° C. to about 120° C., although other reaction temperatures previously mentioned may be employed. The alkylene glycol containing mixture may then be removed from the reactor and separated from the activated carbon catalyst using techniques known in the art. In a batch process, any type and form of activated carbon or other carbon suitable for catalyzing hydrolysis may be employed, including any of those types listed previously. For batch processes a powdered type of carbon or activated carbon is typically selected, while powdered activated carbon is most typical. In another embodiment, an activated carbon catalyst material having a particle size of from about 4×10 to about 12×40 is typically selected for use in batch process systems.

In addition to alkylene oxide and water reactants, the disclosed method may be conducted in the presence of other compounds, including organic solvents, such as ethers.

EXAMPLES

The following examples are illustrative and should not be construed as limiting the scope of the invention or claims thereof.

Example 1-Batch Hydrolysis of Ethylene Oxide to Monoethylene Glycol

Selectivity of hydrolysis reactions carried out in the absence of catalyst and in the presence of a variety of catalysts types was investigated. Tested catalysts included sodium carbonate, bicarbonate exchanged resins, and activated carbons. In each case, water and catalyst were charged to a 300 $cm^3$ stainless steel autoclave. The autoclave was flushed several times with nitrogen and then pressured to 160 psig with nitrogen. The reactor was heated to 120° C. with stirring. Ethylene oxide was slowly added from a tank (with a nitrogen pad of at least 800 psig). After all the ethylene oxide had been added, the mixture was stirred for an additional two hours. The reaction mixture was then cooled to ambient temperature, slowly vented, and the contents transferred to a tared bottle. The pH and concentration of water were determined by wet methods. Other products were determined by gas chromotograph. The results are shown in Table 1.

As shown in Table 1, no catalyst was used in experiment 1 and the selectivity to MEG was 67.5%. In the presence of 0.1 g of sodium carbonate, the selectivity drops to 51.7% (Experiment 2). In the presence of 0.2 g sodium carbonate, the selectivity drops even more to 47.5%. These experiments show that soluble alkaline catalysts (which may increase the rate of hydrolysis) decrease the selectivity to the desired MEG.

Experiments 4, 5, 6, and 13 were conducted with a bicarbonate exchanged ion exchange resin as described in "Process for the Preparation of Alkylene Glycols" (Willem George Reman, WO 95/20559). These are denoted in Table 1 as "A-27(HC03)".

Experiments 7, 8, and 9, which were conducted in the presence of different activated carbons (as indicated), also show an increase in the selectivity to MEG compared to Experiment 1, the control, with no catalyst.

Experiment 10 is another control with no catalyst, but here half the ethylene oxide charge of Experiment 1 is used. The ratio of water to ethylene oxide is 10:1 (5:1 in Experiment 1) and hence the selectivity to MEG in Experiment 10 is greater. Experiments 11, 12, 14, 15, and 17 (with the same ratio of ethylene oxide to water as in Experiment 1, but in the presence of activated carbon) show an increase in selectivity to mono-ethylene glycol.

Because of the possibility of selectively absorbing polyols on the carbon, Experiments 18, 19, 20, and 21 were conducted in which the carbon was extracted with methanol and then dried to constant weight. The weight of the dried carbon was about what was charged to the reactor (within experimental error). A gas chromatograph of the combined methanol extracts indicated that polyols (diethylene glycol, triethylene glycol, etc.) were being selectively absorbed on the carbon, but selectivity to monoethylene glycol was still higher than the control with no catalyst.

In Experiments 22 and 23, carbon was extracted with methanol and dried to constant weight to insure that no polyols (diethylene glycol, triethylene glycol, etc.) remained on the carbon. In these two experiments, the methanol extract was combined with the water filtered from the carbon. Using gas chromatography, the results show clearly a higher selectivity to monoethylene glycol in the presence of carbon (87.6% and 89.6%), compared to 82.7% in Experiment 10 (the control, with no catalyst).

Experiments 24, 25, and 26 show the effects of adding acid, in this case phosphoric acid, on the selectivity to monoethylene glycol. There appears to be a smaller effect here on the selectivity than with added sodium bicarbonate soluble base.

TABLE 1

Batch Hydrolysis of Ethylene Oxide to Monoethylene Glycol

| Exp. # | DM Water (g) | DM Water (mole) | Ethylene Oxide (g) | Ethylene Oxide (mole) | Catalyst (ID) | Catalyst (g) | EO Addn. Time (hr) | Hold Time (hr) | Temp. (deg. C.) | Pressure (psig) | Product (g) | Solution pH | Water (%) | Wt. % products by GC MEG | DEG | TEG | tetrEG |
|---|---|---|---|---|---|---|---|---|---|---|---|---|---|---|---|---|---|
| 1 | 180.0 | 10.0 | 88.0 | 2.00 | None | 0.00 | 1.20 | 2.0 | 120 | 160–340 | 271.5 | 8.1 | 51.9 | 67.481 | 25.316 | 6.173 | 0.634 |
| 2 | 180.0 | 10.0 | 88.0 | 2.00 | Sodium Carbonate (Na2CO3) | 0.10 | 1.25 | 2.0 | 120 | 200–265 | 266.6 | 10.8 | 54.6 | 51.757 | 31.447 | 13.598 | 2.735 |
| 3 | 180.0 | 10.0 | 88.0 | 2.00 | Sodium Carbonate (Na2CO3) | 0.20 | 1.20 | 2.0 | 120 | 210–300 | 267.1 | 10.9 | 55.7 | 47.497 | 32.279 | 15.972 | 3.752 |
| 4 | 180.0 | 10.0 | 88.0 | 2.00 | Bicarbonate Exchanged Resin (A-27(HCO3)) | 50.0 | 1.50 | 2.0 | 120 | 260–290 | 307.4 | 10.0 | 57.8 | 82.571 | 14.320 | 1.124 | 0.000 |
| 5 | 180.0 | 10.0 | 88.0 | 2.00 | Bicarbonate Exchanged Resin (A-27(HCO3)) | 25.0 | 1.75 | 2.0 | 120 | 250–290 | 293.2 | 9.6 | 53.7 | 76.913 | 18.772 | 2.407 | 0.000 |
| 6 | 180.0 | 10.0 | 88.0 | 2.00 | Bicarbonate Exchanged Resin (A-27(HCO3)) | 10.0 | 1.33 | 2.0 | 120 | 245–310 | 277.5 | 9.9 | 54.7 | 74.256 | 21.323 | 3.335 | 0.181 |
| 7 | 180.0 | 10.0 | 88.0 | 2.00 | Coconut Carbon (TIGG CC 1230) | 50.0 | 2.00 | 2.0 | 120 | 190–300 | 323.3 | 8.9 | 54.6 | 74.477 | 22.543 | 2.487 | 0.000 |
| 8 | 180.0 | 10.0 | 88.0 | 2.00 | Acid Washed Carbon (TIGG AWC 1240) | 50.0 | 2.00 | 2.0 | 120 | 280–235 | 315.4 | 2.7 | 54.9 | 74.131 | 22.213 | 3.301 | 0.000 |
| 9 | 180.0 | 10.0 | 88.0 | 2.00 | Norit RO 0.8 | 50.0 | 2.00 | 2.0 | 120 | 260–335 | 317.3 | 9.4 | 55.5 | 74.028 | 22.551 | 3.139 | 0.000 |
| 10 | 180.0 | 10.0 | 44.0 | 1.0 | None | 0.0 | 1.0 | 2.0 | 120 | 230–280 | 219.6 | 6.8 | 72.2 | 82.672 | 15.478 | 1.465 | 0.000 |
| 11 | 180.0 | 10.0 | 44.0 | 1.0 | Coconut Carbon (TIGG CC 1230) | 50.0 | 0.7 | 2.0 | 120 | 240–290 | 269 | 9.0 | 75.8 | 81.779 | 16.846 | 1.207 | 0.000 |
| 12 | 180.0 | 10.0 | 44.0 | 1.0 | Norit RO 0.8 | 50.0 | 1.0 | 2.0 | 120 | 240–290 | 267.9 | 9.3 | 74.9 | 89.888 | 9.661 | 0.000 | 0.000 |
| 13 | 180.0 | 10.0 | 44.0 | 1.0 | Bicarbonate Exchanged Resin (A-27(HCO3)) | 40.0 | 0.4 | 2.0 | 120 | 230–280 | 252.9 | 9.9 | 74.1 | 91.799 | 6.429 | 0.124 | 0.000 |
| 14 | 180.0 | 10.0 | 44.0 | 1.0 | Coconut Carbon (TIGG CC 1230) | 100.0 | 0.7 | 2.0 | 120 | 230–320 | 306.0 | 9.0 | 79.4 | 99.393 | 0.607 | 0.000 | 0.000 |
| 15 | 180.0 | 10.0 | 44.0 | 1.0 | Norit RO 0.8 | 100.0 | 0.7 | 2.0 | 120 | 230–280 | 296.1 | 10.5 | 75.6 | 95.404 | 4.284 | 0.000 | 0.000 |
| 16 | 180.0 | 10.0 | 44.0 | 1.0 | None | 0 | 1.1 | 2.0 | 120 | 235–300 | 229.5 | 6.2 | 69.2 | 81.572 | 16.361 | 1.390 | 0.000 |
| 17 | 180.0 | 10.0 | 44.0 | 1.0 | Norit RO 0.8 | 150.0 | 0.8 | 2.0 | 120 | 230–265 | 354.1 | 10.8 | 79.1 | 95.166 | 4.339 | 0.000 | 0.000 |

TABLE 1-continued

Batch Hydrolysis of Ethylene Oxide to Monoethylene Glycol

| Exp. # | DM Water (g) | DM Water (mole) | Ethylene Oxide (g) | Ethylene Oxide (mole) | Catalyst (ID) | Catalyst (g) | EO Addn. Time (hr) | Hold Time (hr) | Temp. (deg. C.) | Pressure (psig) | Product (g) | Solution pH | Water (%) | MEG | DEG | TEG | tetrEG |
|---|---|---|---|---|---|---|---|---|---|---|---|---|---|---|---|---|---|
| 18 | 180.0 | 10.0 | 44.0 | 1.0 | Norit RO 0.8 (Wash Carbon 3 × MeOH) | 100.0 | 1.1 | 2.0 | 120 | 235–270 | 307.4 | 9.9 | 72.6 | 92.798 | 6.950 | 0.000 | 0.000 |
| 19 | 180.0 | 10.0 | 46.0 | 1.0 | H + TIGG CC Wash with MEOH (combined) | 100.0 | 0.5 | 2.0 | 120 | 225–270 | 314.9 | 11.1 | 33.4 | 84.693 | 14.788 | 0.454 | 0.000 |
|  |  |  |  |  |  |  |  |  |  |  |  | 6.7 | 31.0 | 90.668 | 9.332 | 0.000 | 0.000 |
| 20 | 180.0 | 10.0 | 45.0 | 1.0 | Coconut Carbon (TIGG CC 1230) Wash with MEOH (combined) | 100.0 | 0.8 | 2.0 | 120 | 230–280 | 316.8 | 10.8 | 38.9 | 93.183 | 6.817 | 0.000 | 0.000 |
| 21 | 180.0 | 10.0 | 45.0 | 1.0 | H + TIGG CC Wash with MEOH (combined) | 100.0 | 0.8 | 2.0 | 120 | 230–290 | 311.1 | 7.4 | 34.7 | 90.226 | 9.547 | 0.000 | 0.000 |
| 22 | 180.0 | 10.0 | 45.0 | 1.0 | Norit RO 0.8 Acid Washed with Phosphoric Acid | 100.0 | 1.4 | 2.0 | 120 | 235–280 | 291.7 | 10.7 | 32.2 | 87.576 | 12.051 | 0.373 | 0.000 |
| 23 | 180.0 | 10.0 | 47.0 | 1.1 |  | 100.0 | 0.7 | 2.0 | 120 | 230–290 | 308.1 | 7.0 | 27.4 | 89.635 | 10.365 | 0.000 | 0.000 |
| 24 | 180.0 | 10.0 | 44.0 | 1.0 | Phosphoric Acid (H3PO4 85%) (H + Norit RO) | 0.1 | 0.5 | 2.0 | 120 | 230–290 | 218.5 | 4.1 | 72.2 | 84.517 | 14.657 | 0.827 | 0.000 |
| 25 | 180.0 | 10.0 | 44.0 | 1.0 | Phosphoric Acid (H3PO4 85%) | 0.2 | 1.0 | 2.0 | 120 | 230–260 | 225.9 | 2.3 | 67.7 | 83.032 | 15.623 | 1.331 | 0.000 |
| 26 | 180.0 | 10.0 | 44.0 | 1.0 | Phosphoric Acid (H3PO4 85%) | 0.5 | 0.25 | 2.0 | 120 | 225–260 | 220.2 | 2.4 | 70.2 | 85.367 | 13.788 | 0.845 | 0.000 |

DM Water = demineralized water

Example 2-Continuous Hydrolysis of Ethylene Oxide to Monoethylene Glycol

Various types of activated carbon catalysts were evaluated in an upflow 316 stainless steel "DOWTHERM" jacketed reactor vessel. In each case, 600 cm$^3$ of activated carbon was charged to the reactor vessel. A mixture of ethylene oxide and water was prepared just before each run. In each case, at least a two hour pre-run was performed prior to sample collection. The results are shown in Table 2.

In Table 2, Experiments 1–15 were conducted with a TIGG activated coconut carbon "as-is". As shown, the experiments were conducted primarily at around 300 psig reactor pressure and at temperatures of between 80° C. and 120° C., space velocities of about 1–2 grams/(cm$^3$ of catalyst)(hr) and ethylene oxide to water ratios of 1:10 to 1:20. As shown, selectivity to monoethylene glycol ranged from 84.5% to 100%.

Experiments 18–31 of Table 2 were conducted with an acid washed carbon. For this series of experiments, the carbon was washed by pumping a dilute solution of phosphoric acid (5%) through the carbon bed for several hours, followed by pumping water through the column for several hours. These experiments were conducted at about 300 psig reactor pressure, 80° C.–140° C. temperatures, space velocities of about 0.5–2 grams/(cm of catalyst)(hr) and ethylene oxide to water ratios of 1:20. Selectivity to monoethylene glycol ranged from 86.3–97.6%.

TABLE 2

Continuous Hydrolysis of Ethylene Oxide to Monoethylene Glycol

| Exp # | Catalyst | Molar Ratio EO/H2O | Flow Rate (g/hr) | Time (hr) | Tot. Time (hr) | Temperature, Deg. C., inches from bottom | | | | | Dowtherm Temp (°C.) | Reactor Pressure (psig) | Wt. Tank (g) | Wt. Liq. (g) | H2O (Wt. %) | pH | Products, Wt. %, H2O free | | | | |
|---|---|---|---|---|---|---|---|---|---|---|---|---|---|---|---|---|---|---|---|---|---|
| | | | | | | 5 | 10 | 17 | 24 | | | | | | | | MEG | DEG | TEG | TetEG |
| 1 | TIGG coconut C 1230 | 1/10 | 1270 | 2.5 | 4.5 | 118 | 130 | 132 | 118 | 125 | 486 | 3152 | 3140 | 74.5 | 9.9 | 85.376 | 13.558 | 1.065 | 0.000 |
| 2 | TIGG coconut C 1230 | 1/10 | 1242 | 2.5 | 9.0 | 121 | 131 | 134 | 118 | 125 | 300 | 3074 | 3063 | 72.9 | 9.0 | 85.696 | 13.335 | 0.969 | 0.000 |
| 3 | TIGG coconut C 1230 | 1/10 | 1256 | 2.5 | 13.5 | 116 | 128 | 132 | 118 | 124 | 300 | 3116 | 3095 | 74.5 | 7.0 | 87.742 | 11.749 | 0.509 | 0.000 |
| 4 | TIGG coconut C 1230 | 1/10 | 1287 | 2.0 | 17.5 | 114 | 125 | 130 | 116 | 122 | 301 | 2546 | 2534 | 74.5 | 8.9 | 87.119 | 12.088 | 0.793 | 0.000 |
| 5 | TIGG coconut C 1230 | 1/10 | 1042 | 0.4 | 19.9 | 95 | 98 | 100 | 90 | 99 | 2105 | 329 | 329 | 79.2 | 9.9 | 96.433 | 3.567 | 0.000 | 0.000 |
| 6 | TIGG coconut C 1230 | 1/10 | 1174 | 2.25 | 24.2 | 90 | 97 | 100 | 97 | 100 | 303 | 2614 | 2536 | 79.3 | 9.8 | 95.496 | 4.504 | 0.000 | 0.000 |
| 7 | TIGG coconut C 1230 | 1/10 | 1172 | 2.2 | 28.4 | 71 | 76 | 79 | 77 | 80 | 295 | 2519 | 2462 | 80.5 | 9.7 | 100.000 | 0.000 | 0.000 | 0.000 |
| 8 | TIGG coconut C 1230 | 1/10 | 1177 | 2.1 | 32.5 | 106 | 117 | 124 | 111 | 120 | 302 | 2426 | 2412 | 75.7 | 9.3 | 88.400 | 11.049 | 0.551 | 0.000 |
| 9 | TIGG coconut C 1230 | 1/10 | 1182 | 2.25 | 36.8 | 107 | 118 | 124 | 111 | 122 | 297 | 2640 | 2627 | 75.2 | 8.9 | 88.220 | 11.170 | 0.605 | 0.000 |
| 10 | TIGG coconut C 1230 | 1/10 | 592 | 2.0 | 40.8 | 78 | 80 | 80 | 74 | 80 | 267 | 1173 | 1163 | 79.1 | 8.6 | 89.301 | 8.412 | 2.287 | 0.000 |
| 11 | TIGG coconut C 1230 | 1/10 | 615 | 2.2 | 45.0 | 98 | 100 | 101 | 88 | 99 | 286 | 1246 | 1237 | 77.2 | 8.9 | 92.904 | 7.096 | 0.000 | 0.000 |
| 12 | TIGG coconut C 1230 | 1/10 | 539 | 4.0 | 51.0 | 127 | 128 | 128 | 128 | 120 | 126 | 2350 | 2341 | 73.0 | 7.7 | 82.477 | 15.393 | 2.103 | 0.000 |
| 13 | TIGG coconut C 1230 | 1/20 | 582 | 3.5 | 56.5 | 79 | 80 | 81 | 75 | 80 | 300 | 2027 | 2019 | 88.2 | 8.0 | 89.344 | 7.376 | 3.280 | 0.000 |
| 14 | TIGG coconut C 1230 | 1/20 | 615 | 3.7 | 60.2 | 100 | 101 | 102 | 91 | 100 | 264 | 2339 | 2318 | 85.7 | 8.0 | 94.659 | 5.341 | 0.000 | 0.000 |
| 15 | TIGG coconut C 1230 | 1/20 | 585 | 3.3 | 63.5 | 125 | 125 | 123 | 107 | 120 | 300 | 1955 | 1948 | 83.8 | 7.7 | 90.625 | 9.085 | 0.289 | 0.000 |
| 16 | TIGG coconut C 1230 | 1/20 | 292 | 4.0 | 6.0 | 81 | 81 | 81 | 72 | 79 | 232 | 1606 | 1603 | 87.8 | 2.7 | 94.806 | 5.194 | 0.000 | 0.000 |
| 17 | TIGG coconut C 1230 Washed with H3PO4 | 1/20 | 278 | 2.2 | 10.2 | 103 | 102 | 102 | 88 | 100 | 280 | 1499 | 1494 | 84.6 | 3.5 | 89.517 | 10.483 | 0.000 | 0.000 |
| 18 | TIGG coconut C1230 Washed with H3PO4 | 1/20 | 276 | 4.0 | 16.2 | 124 | 122 | 121 | 104 | 120 | 300 | 1368 | 1364 | 84.3 | 3.0 | 86.836 | 12.391 | 0.773 | 0.000 |

TABLE 2-continued

Continuous Hydrolysis of Ethylene Oxide to Monoethylene Glycol

| Exp # | Catalyst | Molar Ratio EO/H₂O | Flow Rate (g/hr) | Time (hr) | Tot. Time (hr) | Temperature, Deg. C., inches from bottom | | | | | Dowtherm Temp (°C.) | Reactor Pressure (psig) | Wt. Tank (g) | Wt. Liq. (g) | H2O (Wt. %) | pH | Products, Wt. %, H₂O free | | | | |
|---|---|---|---|---|---|---|---|---|---|---|---|---|---|---|---|---|---|---|---|---|---|
| | | | | | | 5 | 10 | 17 | 24 | | | | | | | | MEG | DEG | TEG | Tet.EG |
| 19 | TIGG coconut C 1230 Washed with H3PO4 | 1/20 | 282 | 5.0 | 23.2 | 144 | 140 | 140 | 119 | 140 | 300 | 1403 | 1398 | 83.1 | 3.0 | 87.621 | 11.500 | 0.880 | 0.000 |
| 20 | TIGG coconut C 1230 Washed with H3PO4 | 1/20 | 576 | 4.0 | 29.2 | 80 | 81 | 81 | 74 | 80 | 300 | 2298 | 2291 | 86.3 | 5.0 | 88.577 | 8.050 | 3.373 | 0.000 |
| 21 | TIGG coconut C 1230 Washed with H3PO4 | 1/20 | 606 | 4.0 | 35.2 | 101 | 103 | 103 | 91 | 100 | 300 | 2432 | 2424 | 84.4 | 7.8 | 91.801 | 7.837 | 0.362 | 0.000 |
| 22 | TIGG coconut C 1230 Washed with H3PO4 | 1/20 | 606 | 4.0 | 41.2 | 131 | 130 | 128 | 111 | 124 | 300 | 2428 | 2422 | 83.3 | 7.5 | 89.549 | 9.940 | 0.511 | 0.000 |
| 23 | TIGG coconut C 1230 Washed with H3PO4 | 1/20 | 604 | 4.0 | 47.2 | 152 | 146 | 141 | 122 | 140 | 300 | 2252 | 2238 | 82.7 | 4.8 | 89.223 | 10.189 | 0.588 | 0.000 |
| 24 | TIGG coconut C 1230 Washed with H3PO4 | 1/20 | 1188 | 1.0 | 49.7 | 74 | 78 | 80 | 75 | 80 | 299 | 1786 | 1780 | 83.4 | 7.5 | 97.208 | 2.792 | 0.000 | 0.000 |
| 25 | TIGG coconut C 1230 Washed with H3PO4 | 1/20 | 1204 | 1.5 | 52.7 | 94 | 99 | 102 | 94 | 100 | 298 | 1813 | 1805 | 87.7 | 8.1 | 97.592 | 2.408 | 0.000 | 0.000 |
| 26 | TIGG coconut C 1230 Washed with H3PO4 | 1/20 | 1202 | 1.5 | 55.7 | 118 | 125 | 128 | 115 | 120 | 293 | 1811 | 1807 | 84.4 | 6.1 | 91.758 | 8.215 | 0.000 | 0.000 |
| 27 | TIGG coconut C 1230 Washed with H3PO4 | 1/20 | 1202 | 1.5 | 58.7 | 154 | 154 | 149 | 125 | 140 | 301 | 1811 | 1807 | 83.3 | 5.1 | 90.375 | 9.267 | 0.376 | 0.000 |
| 28 | TIGG coconut C 1230 Washed with H3PO4 | 1/20 | 791 | 3.0 | 63.2 | 89 | 91 | 92 | 83 | 90 | 300 | 2387 | 2380 | 86.2 | 7.8 | 94.709 | 5.291 | 0.000 | 0.000 |

TABLE 2-continued

Continuous Hydrolysis of Ethylene Oxide to Monoethylene Glycol

| Exp # | Catalyst | Molar Ratio EO/H$_2$O | Flow Rate (g/hr) | Time (hr) | Tot. Time (hr) | Temperature, Deg. C., inches from bottom | | | | Dowtherm Temp (°C.) | Reactor Pressure (psig) | Wt. Tank (g) | Wt. Liq. (g) | H$_2$O (Wt. %) | pH | Products, Wt. %, H2O free | | | |
|---|---|---|---|---|---|---|---|---|---|---|---|---|---|---|---|---|---|---|---|
| | | | | | | 5 | 10 | 17 | 24 | | | | | | | MEG | DEG | TEG | Tet.EG |
| 29 | TIGG coconut C 1230 Washed with H3PO4 | 1/20 | 774 | 2.8 | 67.5 | 99 | 102 | 103 | 87 | 100 | 300 | 2344 | 2338 | 85.2 | 8.5 | 95.506 | 4.496 | 0.000 | 0.000 |
| 30 | TIGG coconut C 1230 Washed with H3PO4 | 1/20 | 808 | 2.5 | 71.5 | 110 | 114 | 115 | 99 | 110 | 300 | 2021 | 2016 | 84.7 | 8.6 | 93.287 | 6.713 | 0.000 | 0.000 |
| 31 | TIGG coconut C 1230 Washed with H3PO4 | 1/20 | 989 | 2.0 | 75.0 | 86 | 90 | 91 | 84 | 90 | 300 | 1972 | 1963 | 87.4 | 8.7 | 97.575 | 2.425 | 0.000 | 0.000 |

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed compositions and methods may be utilized in various combinations and/or independently. Thus the invention is not limited to only those combinations shown herein, but rather may include other combinations.

What is claimed is:

1. A process for preparing alkylene glycols, comprising combining alkylene oxide with water in the presence of carbon, wherein said carbon catalyzes the reaction of said alkylene oxide with said water to form alkylene glycol.

2. The process of claim 1, wherein said carbon comprises activated carbon.

3. The process of claim 1, wherein said carbon is present in a particulate form.

4. The process of claim 2, wherein said activated carbon comprises acid-washed activated carbon.

5. The process of claim 1, wherein said alkylene glycol comprises monoethylene glycol, monopropylene glycol, or mixtures thereof; and wherein said alkylene oxide comprises ethylene oxide, propylene oxide, or mixtures thereof.

6. The process of claim 1, wherein said alkylene oxide and water are combined in a continuous reaction process.

7. Alkylene glycol prepared according to the process of claim 1.

8. A process for preparing alkylene glycol products, comprising combining alkylene oxide with water in the presence of a catalyst material comprising activated carbon, wherein said activated carbon catalyzes the reaction of said alkylene oxide with said water to form alkylene glycol product.

9. The process of claim 8, wherein said alkylene glycol product comprises greater than about 70% monoalkylene glycol.

10. The process of claim 8, wherein said activated carbon comprises at least one of coconut carbon, peat carbon, coal carbon, or mixtures thereof.

11. The process of claim 8, wherein said activated carbon has an internal surface area of from about 500 g/m$^2$ to about 1500 g/m$^2$.

12. The process of claim 8, wherein said alkylene oxide and water are combined in a continuous reaction process, and wherein said activated carbon is present in a particulate form.

13. The process of claim 8, wherein said activated carbon comprises acid-washed activated carbon.

14. The process of claim 8, wherein said alkylene glycol comprises monoethylene glycol and wherein said alkylene oxide comprises ethylene oxide.

15. The process of claim 8, wherein said alkylene oxide and said water are combined in a molar ratio of from about 1:5 to about 1:20, at a temperature of from about 60° C. to about 160° C., and at a pressure of from about 100 psig to about 1000 psig.

16. Alkylene glycol product prepared according to the process of claim 8.

17. A process for preparing alkylene glycol products, comprising combining ethylene oxide with water in the presence of activated carbon material wherein said activated carbon material catalyzes the reaction of said ethylene oxide with said water to form an alkylene glycol product.

18. The process of claim 17, wherein said alkylene glycol product comprises greater than about 70% monoethylene glycol.

19. The process of claim 17, wherein said ethylene oxide and water are combined in a continuous reaction process.

20. The process of claim 17, wherein said activated carbon has an internal surface area of from about 500 g/m$^2$ to about 1500 g/m$^2$.

21. The process of claim 17, wherein said ethylene oxide and said water are combined in a molar ratio of from about 1:5 to about 1:20, at a temperature of from about 60° C. to about 160° C., and at a pressure of from about 100 psig to about 1000 psig.

22. Alkylene glycol product prepared according to the process of claim 17.

* * * * *